United States Patent
Tichý

(10) Patent No.: US 8,762,168 B2
(45) Date of Patent: Jun. 24, 2014

(54) METHOD OF DEFINING THE PHYSICAL CONDITION LEVEL

(76) Inventor: Tomáš Tichý, Hronov (CZ)

(*) Notice: Subject to any disclaimer, the term of this patent is extended or adjusted under 35 U.S.C. 154(b) by 307 days.

(21) Appl. No.: 13/262,432

(22) PCT Filed: Mar. 23, 2010

(86) PCT No.: PCT/CZ2010/000032
§ 371 (c)(1),
(2), (4) Date: Sep. 30, 2011

(87) PCT Pub. No.: WO2010/111976
PCT Pub. Date: Oct. 7, 2010

(65) Prior Publication Data
US 2012/0035950 A1 Feb. 9, 2012

(30) Foreign Application Priority Data

Apr. 1, 2009 (CZ) .................... PV2009-205

(51) Int. Cl.
*G06Q 10/00* (2012.01)
*G06Q 50/22* (2012.01)

(52) U.S. Cl.
CPC ...................... *G06Q 50/22* (2013.01)
USPC ............................................ 705/2

(58) Field of Classification Search
CPC ........................................ G06Q 50/22–50/24
USPC ............................. 705/2–3; 600/546
See application file for complete search history.

(56) References Cited

U.S. PATENT DOCUMENTS

| | | | | |
|---|---|---|---|---|
| 5,335,188 A | * | 8/1994 | Brisson | 702/163 |
| 5,361,775 A | * | 11/1994 | Remes et al. | 600/546 |
| 5,752,521 A | * | 5/1998 | Dardik | 600/520 |
| 5,853,351 A | * | 12/1998 | Maruo et al. | 482/8 |
| 6,529,771 B1 | * | 3/2003 | Kieval et al. | 600/509 |
| 7,670,263 B2 | * | 3/2010 | Ellis et al. | 482/8 |
| 7,722,503 B1 | * | 5/2010 | Smith et al. | 482/8 |
| 2004/0103146 A1 | * | 5/2004 | Park | 709/204 |
| 2006/0079800 A1 | * | 4/2006 | Martikka et al. | 600/546 |
| 2006/0136173 A1 | * | 6/2006 | Case et al. | 702/182 |
| 2007/0032733 A1 | * | 2/2007 | Burton | 600/509 |
| 2007/0208531 A1 | * | 9/2007 | Darley et al. | 702/142 |
| 2007/0219059 A1 | * | 9/2007 | Schwartz et al. | 482/8 |

(Continued)

FOREIGN PATENT DOCUMENTS

EP          1402817 A1 *   3/2004

OTHER PUBLICATIONS

International Search report corresponding to International Application No. PCT/CZ2010/000032, dated Sep. 6, 2010.

*Primary Examiner* — Robert Sorey
(74) *Attorney, Agent, or Firm* — Renner, Otto, Boisselle & Sklar, LLP.

(57) ABSTRACT

The method of defining the physical condition level, in particular the method of defining the physical condition level for men, under which first the parallel measuring of heart rate, organism performance, and measuring or evaluation of other parameters influencing physical performance take place using a measuring device, and subsequently the measuring or evaluating device forms a database containing at least two records that include a set pairs of the heart rate and organism performance values measured at the same time and arranged in that record chronologically.

7 Claims, 2 Drawing Sheets

(56) References Cited

U.S. PATENT DOCUMENTS

Figure 1:
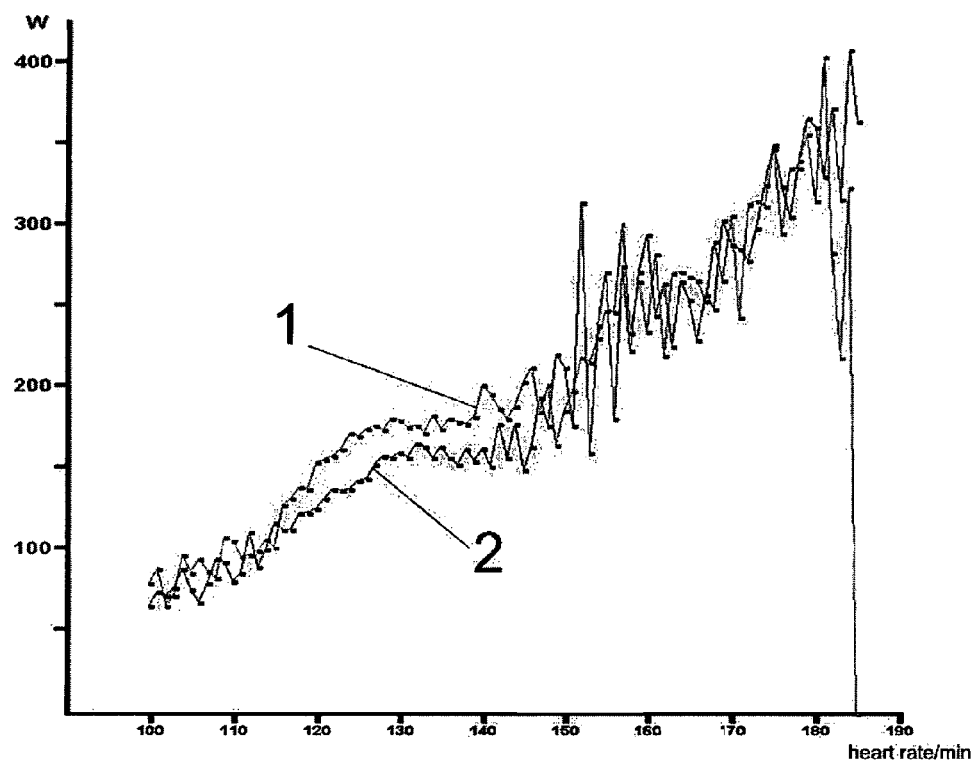

| | | |
|---|---|---|
| 2009/0011907 A1* | 1/2009 | Radow et al. .................. 482/57 |
| 2009/0069156 A1* | 3/2009 | Kurunm ki et al. ............... 482/9 |
| 2009/0170660 A1* | 7/2009 | Miglioranza .................... 482/1 |
| 2009/0312998 A1* | 12/2009 | Berckmans et al. ............ 703/11 |
| 2010/0216601 A1* | 8/2010 | Saalasti et al. .................... 482/8 |
| 2010/0235195 A1* | 9/2010 | Firminger et al. ............... 705/3 |

* cited by examiner

US 8,762,168 B2

METHOD OF DEFINING THE PHYSICAL CONDITION LEVEL

This application is a national phase of International Application No. PCT/CZ2010/000032 filed Mar. 23, 2010 and published in the English Language.

TECHNOLOGY AREA

The invention relates to the method of defining the physical condition level, in particular the method of defining the physical condition level for men, in which first the parallel measuring of heart rate, performance of the organism, and measuring and evaluation of other parameters influencing physical performance take place.

STATE-OF-THE-ART

A whole series of procedures is currently used for defining manpower measuring, and they are realised in both, stationary laboratory facilities and portable facilities.

Well-known procedures are for example those, which use simple calculation models based on the analysis of the speed and heart rate measured, or the pedalling rate, for defining the level of the physical performance of a bicyclist. These performance parameters are usually monitored in predefined time intervals. These methods are not quite accurate and bring orientation outputs only.

Much more accurate outputs are brought by facilities capable of, in addition to above variables, measuring the performance of the individual monitored. The performance is usually set in watts, and subsequently evaluated using various calculation models that assess individual performance, but are also capable of evaluating and comparing performance of the individual in various time periods.

For example the lactate test or spiro-ergonomic test belongs to well-known methods used for evaluation of the physical condition level. Using these tests, the heart rate scale of the individual can be divided into zones. Each zone represents certain specific physiological and biochemical processes running in the organism. It is in particular the rate of energetic processes engagement in the organism, forming final energy, based on which individual muscles may operate within the organism. In addition, for example individual zones of the heart rate correspond with certain lactate level in blood. These zones are used in the training process when the individual selects certain training type that corresponds with the specific zone of the heart rate and ranges within this zone during this training.

The level of physical condition may also be determined under the well-known analysis, in which the major variable monitored is the level of fatigue that is defined so that the training is first divided into to parts. In each part, the average performance in watts and the average heart rate are calculated. Ratios between the performance and the heart rate in each part are then calculated, and these two results are divided by each other. Subsequently, results of training units are compared. If deterioration ranges within the value of five percent, the fatigue level is fine. If the result exceeds ten percent, it is relatively a great decline accompanied with greater fatigue.

It is indeed necessary to view the variable in terms of sense, experience, and knowledge. Disadvantage of this analysis consists in the fact that variables are determined by linear method, although scales of both variables are not identical. The result is therefore not much objective. This analysis can only be used in a very limited range in specific cases.

With the current technology, no procedures are known that would bring accurate answers to questions, whether the person monitored applies training load to his/her body in the right direction, whether the performance efficiency increases in all factors, which the final racing performance consists of.

A whole series of disadvantages of the current technology is apparent from the above. The objective of this invention is to create a method of defining the level of physical condition that would eliminate as much disadvantages of the current technology as possible.

INVENTION FUNDAMENTALS

It eliminates disadvantages mentioned to a great extent, and invention objectives are met by method of defining the physical condition level, in particular the method of defining the physical condition level for men, under which first the parallel measuring of heart rate, organism performance, and measuring and evaluation of other parameters influencing physical performance take place using a measuring device, and invention fundamentals consist in the fact that the measuring or evaluating device first forms a database containing at least two records that include a set of value pairs of the heart rate and organism performance measured at the same time and arranged in that record chronologically.

Individual record is the specific training of the person monitored that is determined by parallel measuring of variables of the heart rate and performance, which is defined usually in watts (W). Regular watt-meters are for example used for this measuring in bicycle racing. The size of the set of pairs—heart rate and performance—in the specific record is given by length of measuring and the time interval of data recording in the measuring device. The database is understood a set of records that meet requirements of the user who makes use of these analyses. Input requirements might be for example time periods specified in terms of the date, and/or defining the record type such as training of basic persistence, power persistence, warm up before the race, brute strength training, etc.

To obtain more quality outputs, it is beneficial if the record stored in the database contains also information on, the date of measuring and other parameters influencing the physical performance, i.e. parameters of the environment which such physical performance is conducted in, and parameters characterising the health condition of the person evaluated.

Parameters of the environment are understood mainly the air temperature and humidity. For example, at temperatures exceeding 30° C., the heart rate increases mainly due to increased need of thermoregulation of the organism. Parameters characterising the health condition are understood mainly the subjective perception of fatigue, when in case of high fatigue level non-proportional drop of both, the heart rate and mainly the performance, occurs. In other words, if the person is more and highly tired, with the same efforts determined by heart rate, a noticeable watt decline in the organism occurs. Both types of information make interpretation of these analyses more precise with respect to training process management based on the experience and knowledge of the individual in question or his/her trainer.

The database is subsequently processed advantageously by measuring or evaluating device, so that it first groups performance values from the specific record or time period, which have the same value of the heart rate assigned, and then arithmetic means are defined from these performance values, resulting in a set of data pairs representing the specific record from the database, or specific time period containing information on the heart rate and its corresponding average performance. It is beneficial when a curve of dependency of the average performance and the specific heart rate is formed from the set of data pairs using the measuring or evaluating device as follows. It is also beneficial when all pairs of variable values of the heart rate and the performance in all records in the database are transformed into subsets, where each subset contains all performance values from all records with identical value of the heart rate. Aggregation of values along the scale of the heart rate variable is made. Interpretation of the curve of dependency of the average performance and the specific heart rate is as follows. If for example the value of 120 heart-beats per minute corresponds with the average performance of 200 W, it means that in average the performance of the individual in question at the heart rate of 120 heart-beats per minute was 200 W.

With respect to the highest level of objectiveness, it is necessary to compare identical types of records. Records compared should have identical histograms of the heart rate to the maximum extent possible. This can be achieved based on comparison of identical record types only. It is therefore beneficial, if the measuring or evaluating device performs filtration of the set of data pairs of the specific record or the specific time period, so that at least two sets of data pairs of the specific record or time period having the same parameters influencing the physical performance are filtered out. The time period selected might be non-continuous.

It is also beneficial when the values of at least two sets of data pairs of the specific record or time period are displayed by measuring or evaluating device as a graphic curve, so that the x-coordinate contains corresponding value of the average performance, and the frequency value of individual average performances at the specific heart rate in the specific record is given by sum of basic sets of data pairs, which the values of the heart rate conform in. The difference in positioning individual curves sets the variable level of the physical condition of compared records or compared time periods; in other words, higher level of the physical condition is represented by set of data pairs that is in this diagram represented by curve with higher position. The same heart rate value corresponds with higher average performance.

In the next step, the measuring or evaluating device selects one of the sets of data pairs that is visually presented by specific curve representing the specific record or time period, and its performance values are defined as zero with the result that at least one other set of data pairs from another record or time period is assigned to it, and the difference of average performance values is defined and graphically displayed, and a set of pairs containing values of the heart rate and differences of individual average performances of specific records or time periods compared at the same heart rate is formed.

The measuring or evaluating device then sets the value of the weighted arithmetic mean from differences of individual average values, and each difference of individual average performance values at the specific heart rate between two monitored records is count towards the weighted arithmetic mean so many times how many times the sum of frequencies of sets of performance pairs and the specific heart rate is included in both records or time periods compared. The unit of the weighted arithmetic average value is W/1 heart-beat, and interpretation of this unit is as follows.

We compare two records that represent two particular trainings of the same type between each other, and if the first record is better by 20 W/1 heart-beat than the other one, it means that in average the first one was better by 20 W, no matter whether we compare the $5^{th}$ minute or the $93^{rd}$ minute in both records, or whether we assess the level of performance at 119 heart-beats per minute or 120 heart-beats per minute.

The deviation against the difference of average performances between two records is as follows. No better record can be defined from the average performance with respect to defining the physical performance level, since we do not know the efforts leading to these average performances. And just in the unit W/1 heart-beat, the efforts are incorporated as the heart rate that led to the average performance throughout the entire record. From the physiological point of view, the man who performs better at the same heart rate than in the previous period has higher level of physical performance.

This procedure transforms average performances between two compared records or time periods with different heart rates into average performances with the same average value of the heart rate. Upon such transformation, we may set the difference of average performances between two compared records or time periods, which indicates different levels of the physical condition. Average performances are converted to the same unit of exerted efforts, which is the performance per 1 heart-beat (W/1 heart-beat).

From the set of compared records, the measuring or evaluating device shall select one that is assigned a value of 0 W/1 heart-beat, and remaining records are compared with this sample record, so that they are assigned respective value of the unit W/1 heart-beat, and then the best record is selected and compared again, and all other records are assigned final values of the unit W/1 heart-beat and all records are then plotted based on the date and value of the unit W/1 heart-beat. The x-coordinate represents the record date, and the y-coordinate contains the value of the weighted arithmetic mean corresponding with this date. Graphic representation shows changes of the physical condition, so that if the curve descends in time, the physical condition level deteriorates and vice versa, if the curve ascends in time, the physical condition level improves.

It is beneficial that the measuring or evaluating device subsequently sets the value of fatigue, and the difference of the actual performance at that time and the average performance, which corresponds to the same heart rate as the actual heart rate at that time, is determined first. Values set are then divided in the time line into two parts, values of the first half (part) of the record and the second half (part) of the record are added separately, and the coefficient of fatigue is defined so that the totalled value of the first half of the record is subtracted from the totalled value of the second half of the record.

With respect to the training process, the fatigue variable is one of the most important for modelling the training load. The training load causes fatigue of the organism, which on a basis of physiological regeneration processes leads to positive adaptation to training challenges. Therefore there are efforts, in addition to the subjective fatigue perception, to quantify the level of fatigue in individual records more objectively. From the physiological point of view, fatigue means the following. With increasing fatigue of the organism, the individual must make greater efforts, and the heart rate increases in the endeavour to maintain constant value of the performance. Final fatigue value indicates the following. The more negative value we obtain, the greater was the disproportion between the load evoked and the condition of the organism, which is determined by practicing, training load in previous days, and related fatigue. It results from the above that the unit for both, the curve of the actual fatigue development and the final fatigue value for the specific record, is the performance defined in watts.

In addition, the measuring or evaluating device defines advantageously values of performance development linked to heart rate zones, and one average value from the specific record is determined for each heart rate zone and subsequently shown in the diagram. We can this way analyse performance development for individual heart rate zones of individual records in chronological sequence. Based on this analysis, we can monitor the course of structure of individual training types, and based on this feedback we are able to modify the training plan with the objective to increase the quality of the entire training system.

Unlike load tests applied by professional athlete few times a year only, we can use these analyses after each training session and have an immediate feedback. The highest added value for analysing the training process based on these analyses is the fact that analysing the course of individual training types within the period examined is made on a basis of comparing variables of the heart rate and the watt performance of the individual in question. If the individual achieves higher performance than in the previous period, it achieves higher values of the watt performance at the same values of the heart rate, which is determined mainly by the level of efforts exerted.

The method of defining physical condition level under this invention enables to create continuous feedback on the development of physical condition and fatigue level. Unlike the well-known state of the technology, it enables higher level of objectivity for defining performance development, based on comparing variables of the heart rate and the watt performance. Another advantage is the possibility to monitor the structure of watt performance for individual heart rate zones in individual training types in the period monitored. The method of defining physical condition level under this invention also increases significantly the level of objectivity with respect to monitoring of fatigue development in individual records and with respect to monitoring of the fatigue evoked by training load in entire periods.

REVIEW OF FIGURES IN THE DRAWING

The invention will be explained better by drawing, in which

Figure 2:
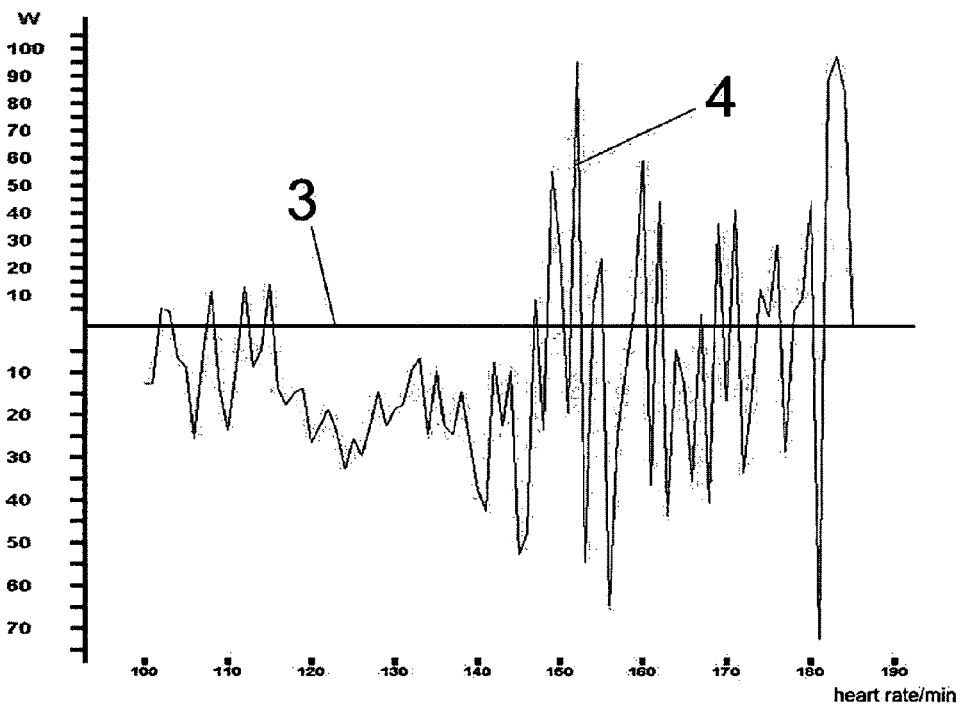
Figure 3:
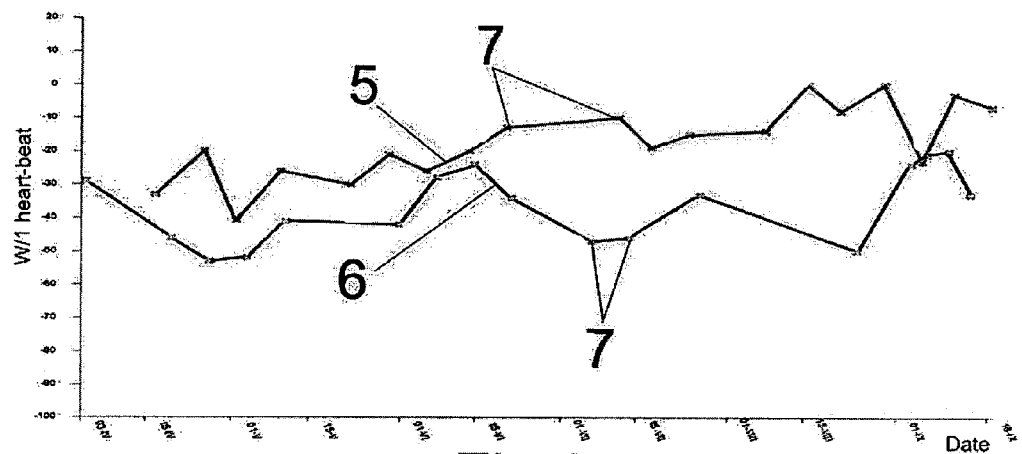
Figure 4:
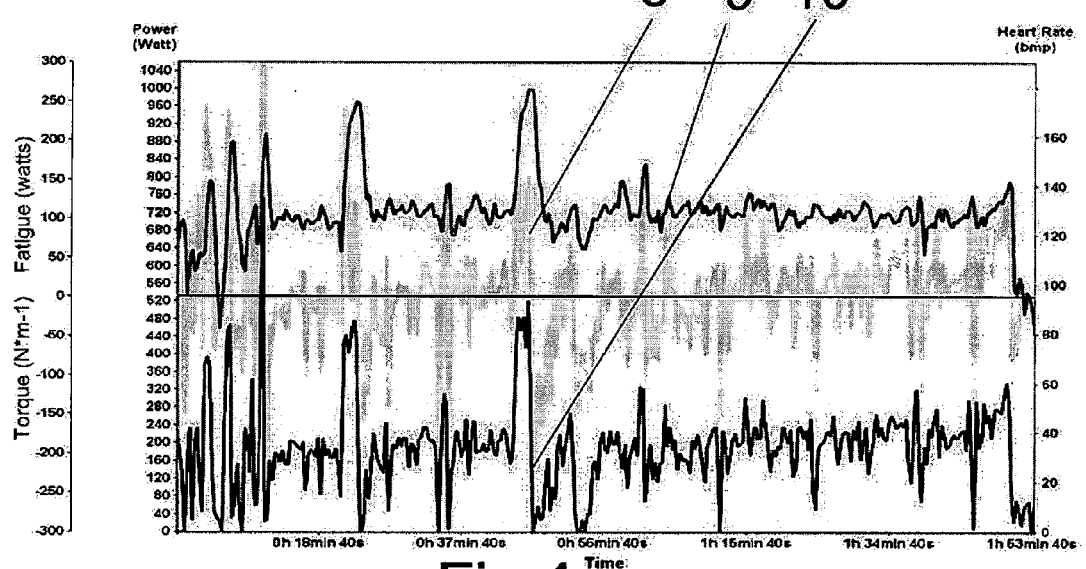
Figure 5:
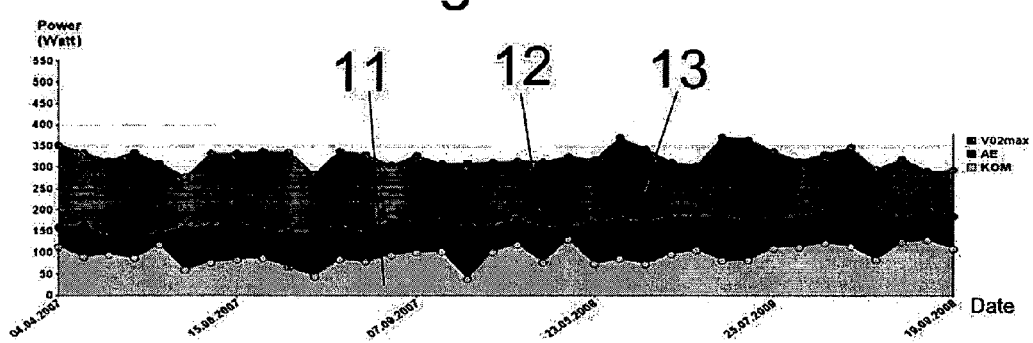

FIG. 1 shows an analytical diagram of dependency of the watt performance on the heart rate for two particular periods, FIG. 2 shows an analytical diagram of dependency of the watt performance on the heart rate with respect to watt differences, FIG. 3 shows an analytical diagram of performance W/1 heart-beat, FIG. 4 shows an analytical diagram of fatigue, and FIG. 5 shows an analytical diagram of the watt development for individual heart rate zones.

EXAMPLE OF INVENTION UTILISATION

According to the method of defining the physical condition level of men, the measuring devise first performs repeated parallel measuring of the heart rate, performance of the organism, and measuring or evaluation of other parameters influencing the physical performance.

Values measured are transmitted to a device containing evaluating software. Alternatively, the evaluating software may be part of the measuring device. The same applies in case when measuring is carried out in laboratory conditions and measured values are entered directly to the evaluating software.

The example of invention use describes determination of the physical condition level of the bicyclist, where some of the readily available devices indicated as wattmeter are used for measuring.

From continuous monitoring, a database of measured values was created in the evaluating device. It includes 650 individual records, and these records contain a set of pairs of heart rate values and organism performance, which are measured at the same time with in the interval of 5 seconds, and arranged within the specific record chronologically.

The user then supplements individual records with data containing information on the training date and type, such as the training of basic persistence, power persistence, warm up before the race, brute strength training, etc. Individual records also contain data information on other parameters influencing the physical performance, i.e. parameters of the environment, which the physical performance is carried out in, such as the temperature, pressure, nature of the training route, and parameters characterising health condition of the person evaluated, such as illness, feeling in the training, and the level of training efforts, and this data information is either entered by user or obtained directly from the measuring device.

The database is subsequently processed by software application installed in the evaluating device, based on user's specification, so that it first groups performance values from the specific record or time period that have the same value of the heart rate assigned, and then arithmetic means are defined from these performance values, resulting in a set of data pairs representing the specific record from the database, or specific time period containing information on the heart rate and its corresponding average performance.

From these data pairs, a curve of dependency of the average performance and the specific heart rate is subsequently formed. This curve may be used for evaluating the physical condition level of the individual monitored and can be interpreted that if for example the value of 120 heart-beats per minute corresponds with the average performance of 200 W, it means that in average the performance of the individual in question at the heart rate of 120 heart-beats per minute was 200 W.

The evaluating device then performs filtration of the set of data pairs of the specific record or the specific time period, so that at least two sets of data pairs of the specific record or time period having the same parameters influencing the physical performance are filtered out, and these sets are shown in the diagram (FIG. 1). The diagram enables the analysis of dependency of watt performance on the heart rate for two specific time periods. The x-coordinate represents the heart rate value and the y-coordinate represents its corresponding value of the average performance; the value of frequencies of individual average performances at the specific heart rate in the specific record is given by sum of basic sets of data pairs with identical values of the heart rate.

The first period is shown by curve 1 formed by records from the period of 01.04.2008-01.10.2008, and the load type is indicated as "Warm up before the race". The second period is shown by curve 2 formed by records from the period of 01.04.2007-01.10.2007, and the load type is indicated again as "Warm up before the race".

To explain it, we must say that the individual applies this type of training always one day prior to the race. Since active or passive regeneration takes place only in the course of two days before the race, conditions are almost identical. The only thing that changes is the performance (W) of the individual that depends on his/her actual condition linked to the training process.

It can be figured out from the diagram that the individual monitored showed higher level of the average physical condition in 2008 than in 2007. We can come to this conclusion, if we compare positions of individual curves 1 and 2 within the interval of 110-145 heart-beats per minute, in which this individual spends ca 90% of his/her time. The curve 1 characterising the performance in 2008 is positioned higher, where the value of 120 heart-beats per minute corresponds to the watt performance of 140 W, which means that the average performance of the individual monitored in all records included in this analysis was 140 W at the heart rate of 120 heart-beats per minute. Since the curve 2 from 2007 is positioned lower, it means that the physical condition level was lower in that year. For the value of 120 heart-beats per minute, the performance of the individual monitored was 129 W only. It means that the difference between both periods compared is 11 W at 120 heart-beats per minute. Lower average performance corresponds to the same heart rate value.

In addition, the evaluating device selects one of the of the data pair sets that is presented visually by particular curve representing the specific record or time period, and its performance values are determined as zero, with the result that at least one other set of data pairs of another record or time period is assigned to it and presented visually by other curve, and the difference of average performance values is determined. This will result in a set of pairs containing heart rate values and values of differences of individual average performances of specific records or time periods compared at the same heart rate, which is displayed in the diagram (FIG. 2).

For the zero curve 3, data corresponding to the curve 1 under FIG. 1 have been used. The curve 4 shows the difference of the performance between above periods monitored at 110-145 heart-beats per minute.

Based on the above procedure, the evaluating device calculates the final value of the unit W/1 heart-beat between compared periods. In this case, records of the load type "Warm up before the race" for the period of 01.04.2008-01.10.2008 are better in average by 19 W/1 heart-beats than records from the previous year.

Subsequently, the evaluating devise shall define the value of the weighted arithmetic mean (W/1 heart-beat) from differences of individual average values, and each difference of individual average values at the heart rate specified between two compared records, represented by curves, is included in the weighted arithmetic mean (W/1 heart-beat) so many times, how many times the sum of frequencies of pair sets of the performance and the heart rate is included in both records compared. The first curve has for example for the value of 120 heart-beats per minute the average performance of 200 W, and this performance was calculated from 350 values. The second curve has for the value of 120heart-beats per minute the average performance of 220 W, and this performance was calculated from 300 values. The difference at 120 heart-beats is −20W, if the zero level is represented by second curve, or possibly +20W, if the zero level is represented by first curve. These 20 W are not included in the final value once only, as if the arithmetic mean is used, but 650 times, since the weighted arithmetic mean is used here. The above procedure is carried out for the whole scale of the heart rate.

Values of the weighted arithmetic mean (W/1 heart-beat) between specific records compared are shown graphically by evaluating device as a curve, so that individual curve points represent specific records, and the x-coordinate represents the record date, and the y-coordinate contains corresponding value of the weighted arithmetic mean (W/1 heart-beat) to this date. From the set of compared records, the measuring or evaluating device then selects one, which is assigned a value of 0 W/1 heart-beat, and remaining records are compared with this sample record, so that they are assigned respective value of the unit W/1 heart-beat, then the best record is selected and compared again, and all other records are assigned the final value of the unit W/1 heart-beat, and all records are then plotted based on the date and value of the unit W/1 heart-beat.

The analysis above can be named as W/1 heart-beat performance analysis. The diagram (FIG. 3) shows curves 5 and 6, basic data of which correspond to the load type "Warm up before the race" in 2007 a 2008.

For plasticity, individual trainings in 2007 are connected by curve 6, and trainings in 2008 are connected by curve 5. Each record representing individual training unit is shown in the diagram as a single point 7, and the x-coordinate indicates the date of this training and the y-coordinate the value of the variable W/1 heart-beat as compared with the best record from this set of records.

As already mentioned, the record with the worse performance/heart rate ratio, indicating worse current performance, has a more negative value of the unit W/1 heart-beat.

The above shows changes of the physical condition level, so that if the curve descends in time, the physical condition level deteriorates and vice versa, if the curve ascends in time, the physical condition level improves.

The evaluating device subsequently sets the value of fatigue, and the difference of the actual performance at that time and the average performance, which corresponds to the same heart rate as the actual heart rate at that time, is determined first, and values set are then divided in the time line into two parts, values of the first half (part) of the record and the second half (part) of the record are added separately, and the coefficient of fatigue is defined so that the totalled value of the first half of the record is subtracted from the totalled value of the second half of the record.

We can name the above as fatigue analysis. The evaluating device then displays graphically (FIG. 4) the specific record, which is the training with the load type "Warm up before the race", from Dec. 09, 2008. The diagram (FIG. 4) shows the fatigue curve 8, the heart rate curve 9, and the performance curve 10.

It results from the analysis that the 4 high-intensity short-term intervals were applied in the first half of the training, with the duration from tens of seconds up to a 2-minute interval, in which previously mentioned energetic systems were started up. Upon completion of these intervals, basic persistence in lipometabolism followed only.

The fact that this individual was relaxing the day before this training caused with these intervals great overloading of the organism, which is determined by loss in power at the same heart rate. The average fatigue in the first half of the training ranged around 8 W. In the second half of the training, when the individual was from the heart rate point of view moving in lipometabolism only, the watt performance subsequently increased at the same heart rate. With respect to physiology, positive adaptation was achieved even during this training. The overall fatigue index for this training was +15 W. It means that watt performance of the individual in question in the first half of the training and at the same heart rate was in average lower by 15 W than in the second half of the training, and the already mentioned positive physiological adaptation was experienced that is necessary for achieving the best possible result in the race next day.

From the physiological point of view, fatigue means the following. With increasing fatigue of the organism, the individual must make greater efforts, and the heart rate increases in the endeavour to maintain constant value of the performance.

In addition, the evaluating device defines values of performance development in relation to heart rate zones, and single value from the specific record is set for each heart rate zone; these values are then displayed in the diagram (FIG. 5). We can name this analysis as a performance development analysis for individual heart rate zones. In the diagram (FIG. 5), trainings with the load type "Warm up before the race" are shown for 2007 and 2008. The difference against the performance analysis W/1 heart-beat (FIG. 3) is that here we can analyse the performance structure of individual records with respect to zone 11 of the heart rate for compensation, for zone 12—basic persistence, and for zone 13—VO2max. In the heart rate zone 13—VO2max, it is necessary to spend a few minutes in this type of training in order to start up energetic systems needed for good result in the race next day.

From the diagram (FIG. 5), we can conclude increasing performance for the period 2007 and 2008, since performance values (W) for the heart rate zone 11—compensation and the heart rate zone 12—basic persistence have an increasing trend. We can also experience slightly deteriorated performance for the zone 13—VO2max at the end of the 2008 season, which is caused by the fact that the individual in question had already been tired at the end of the season.

General benefit of this analysis consists in the fact that we can analyse the structure of individual training types within a time period, recognise for example decline in performance for particular heart rate zone, and respond to it by changing the training plan.

INDUSTRIAL APPLICABILITY

The method of defining the physical condition level under the invention can be used for example in analysing and managing the training process for both, professional and amateur athletes.

LIST OF REFERENCE SIGNS

1 curve I
2 curve II
3 zero curve
4 curve III
5 curve IV
6 curve V
7 point
8 fatigue curve
9 heart rate curve
10 performance (power) curve
11 heart rate zone for compensation
12 basic persistence zone
13 VO2max zone

The invention claimed is:

1. A method of defining a physical condition level of a person, comprising:
   using a measuring and evaluating device to perform parallel measuring of i) a heart rate of the person and ii) power output performance of the person during a physical performance;
   measuring and assessing other parameters influencing the physical performance of the person;
   creating, by the measuring and evaluating device, a database containing at least two records, each of which comprise data pair sets including a heart rate value and power output value by the person, respective data pairs being measured at the same time and chronologically arranged within each specific record,
   wherein the at least two records stored in the database comprise i) information on the date of measuring and ii) other parameters influencing the physical performance of the person, the other parameters comprising parameters of the environment in which the physical performance is performed, and parameters characterizing a health condition of the person being evaluated;
   processing, by the measuring and evaluating device, such that power output performance values from a specific record or from a time period including two or more records are grouped based on having an identical heart rate value;
   calculating, by the measuring and evaluating device, an arithmetic mean for each processed group resulting in a data pair set containing each heart rate value and an average power output performance corresponding to each heart rate value;
   filtering, by the measuring and evaluating device, based on the parameters influencing physical performance of the person, the data pair set of the specific record or time period including two or more records into at least two sets of data pairs; and
   displaying, by the measuring and evaluating device, the filtered at least two data pair sets in a diagram representing the dependency of average power output performance on heart rate for two specific time periods for analysis of the physical condition level of the person,
   wherein the x-coordinate of the diagram contains each heart rate value and the y-coordinate of the diagram contains the average power output performance value corresponding to the heart rate value.

2. The method of defining the physical condition level according claim 1, wherein the measuring and evaluating device subsequently selects one of the data pair sets representing the specific record or time period including two or more records, and performance values for the selected data pair set are defined as zero, and at least one other data pair set of another record or time period including two or more records is assigned to the selected data pair set, and a set of pairs is created containing heart rate values and values of differences of individual average performances of specific records or time periods including two or more records compared at the same heart rate.

3. The method of defining the physical condition level according to claim 2, wherein the measuring and evaluating device subsequently defines a value of a weighted arithmetic mean from differences of individual average values at a specific heart rate between two compared records or time periods including two or more records, wherein a number of times the differences are included in the weighted arithmetic mean is based on a number of data pair sets used to define the weighted arithmetic mean.

4. The method of defining the physical condition level according to claim 3, wherein the measuring and evaluating device subsequently selects a single record from the set of compared records that has been assigned the value 0 Watts/1 heart-beat, and remaining records are compared with the selected record such that each is assigned a respective value having the unit Watts/1 heart-beat, and a record having the highest positive value is selected and compared again, and all other records are assigned final values having the unit Watts/1 heartbeat, and all records are then plotted based on the date and value having the unit Watts/1 heart-beat.

5. The method of defining the physical condition level according to claim 1, wherein a frequency of individual average power output performances at a specific heart rate in the specific record or time period including two or more records is given by a sum of basic data pair sets in which heart rate values are identical.

6. The method of defining the physical condition level according to claim 1, wherein the measuring and evaluating device subsequently defines a fatigue value by:
- determining the difference between the actual performance at a specific time and the average performance corresponding to the same heart rate as the actual heart rate at the specific time,
- dividing values in the time line into two parts,
- separately summing values of the first half of the record and values of the second half of the record, and
- defining a coefficient of fatigue as the difference between the summed value of the first half part of the record and the summed value of the second half part of the record.

7. The method of defining the physical condition level according to claim 1, wherein the measuring and evaluating device defines values of performance development in relation to heart rate zones, and a single average value from the specific record or time period including two or more records is determined for each heart rate zone and is subsequently displayed in a diagram.

* * * * *